(12) United States Patent
Tang et al.

(10) Patent No.: US 9,114,371 B2
(45) Date of Patent: Aug. 25, 2015

(54) SYSTEM AND PROCESS FOR MELAMINE PRODUCTION BY GAS-PHASE QUENCHING METHOD OF ENERGY EFFICIENT AND COST SAVING TYPE

(75) Inventors: Yin Tang, Beijing (CN); Zhongwu Yuan, Beijing (CN); Yuande Gong, Beijing (CN); Mingda Yin, Meishan (CN); Xiuzhen Yang, Beijing (CN); Duanyang Chen, Meishan (CN); Jianglin Yi, Meishan (CN); Lin Lei, Meishan (CN); Chaohui Liu, Meishan (CN); Xuchu Li, Meishan (CN); Xikun Xiong, Beijing (CN); Hui Chen, Beijing (CN); Deli Kong, Beijing (CN); Wenmao Jiang, Meishan (CN); Gang Li, Meishan (CN); Lihong Guo, Meishan (CN); Zhongyun Li, Beijing (CN); Guangsong Lan, Shaya County (CN); Guohua Yuan, Beijing (CN); Xiangdong Kuang, Beijing (CN)

(73) Assignees: BEIJING EDGEIN TECHNOLOGY CO., LTD., Beijing (CN); SICHUAN GOLDEN-ELEPHANT SINCERITY CHEMICAL CO., LTD., Meishan (CN)

( * ) Notice: Subject to any disclaimer, the term of this patent is extended or adjusted under 35 U.S.C. 154(b) by 0 days.

(21) Appl. No.: 13/985,647

(22) PCT Filed: Apr. 20, 2012

(86) PCT No.: PCT/CN2012/000538
§ 371 (c)(1),
(2), (4) Date: Aug. 15, 2013

(87) PCT Pub. No.: WO2012/146056
PCT Pub. Date: Nov. 1, 2012

(65) Prior Publication Data
US 2013/0324720 A1 Dec. 5, 2013

(30) Foreign Application Priority Data

Apr. 28, 2011 (CN) .......................... 2011 1 0108644

(51) Int. Cl.
*C07D 251/60* (2006.01)
*B01J 8/18* (2006.01)
(52) U.S. Cl.
CPC ............. *B01J 8/1872* (2013.01); *C07D 251/60* (2013.01)

(58) Field of Classification Search
CPC ............................ C07D 251/60; B01J 8/1872
USPC ................................................. 544/201, 203
See application file for complete search history.

(56) References Cited

U.S. PATENT DOCUMENTS

| 4,451,271 A | 5/1984 | Yamamoto et al. |
| 2010/0222582 A1* | 9/2010 | Kern et al. .................... 544/201 |

FOREIGN PATENT DOCUMENTS

| CN | 1188761 A | 7/1998 |
| CN | 1493565 A | 5/2004 |
| CN | 101822960 A | 9/2010 |
| CN | 101827829 A | 9/2010 |
| CN | 101863848 A | 10/2010 |
| CN | 201971766 U | 9/2011 |
| CN | 102219754 A | 10/2011 |
| WO | WO 2009/050169 A2 | 4/2009 |

OTHER PUBLICATIONS

Jun. 29, 2012 First Office Action issued in Chinese Application No. 201110108644.9 with English-language translation.
Mar. 15, 2013 Second Office Action issued in Chinese Application No. 201110108644.9 with English-language translation.
Aug. 9, 2012 International Search Report issued in International Application No. PCT/CN2012/000538.
Apr. 15, 2014 Office Action issued in Japanese Application No. 2014-506724 (with English Translation).

* cited by examiner

*Primary Examiner* — Venkataraman Balasubramanian
(74) *Attorney, Agent, or Firm* — Oliff PLC

(57) ABSTRACT

A system and process for melamine production by gas-phase quenching method and its process are provided. The said system includes a urea scrubber, after which a fluidized bed reactor, a hot-air cooler, a hot-air filter, a crystallizer and a melamine collector are installed in series successively, where the said melamine collector is connected to the said urea scrubber and the said fluidized bed reactor is connected to a carrier gas pre-heater which is connected to a carrier gas compressor; the said system further includes a gas-liquid separator which is connected to the said urea scrubber which is connected to a crystallizer; wherein a cool air blower is provided between the said gas-liquid separator and the crystallizer. The production system of the invention has the advantages of high productivity, stable operation, low energy consumption, low investment and high economic value of tail gas.

16 Claims, 3 Drawing Sheets

SYSTEM AND PROCESS FOR MELAMINE PRODUCTION BY GAS-PHASE QUENCHING METHOD OF ENERGY EFFICIENT AND COST SAVING TYPE

FIELD OF THE INVENTION

This invention relates to the melamine production field, and more particularly, to a system and process for melamine production by gas-phase quenching method of energy efficient and cost saving type.

BACKGROUND OF THE INVENTION $(NH_2)_3C_3N_3$, with the scientific name melamine, is a kind of widely-used organic chemical material. It is mainly used to synthesize melamine-formaldehyde resin, manufacture daily utensils, decorative veneer, textile finishing agent, etc., mix with diethyl ether to generate paper treating agent. Moreover, it can also be used as environmentally-friendly high-performance coating cross-linking agent, flame retardant material, etc. The dicyandiamide method is adopted to produce melamine in early technology. The specific production process is: use $CaC_2$ to produce $CaCN_2$ which generates dicyandiamide after hydrolysis and dimerization, and then heat and decompose the dicyandiamide to produce melamine. However, the dicyandiamide method has a high cost due to use of calcium carbide, resulting in poor economic performance of melamine production process.

In order to solve the above-mentioned defects, the dicyandiamide method was replaced by the urea method gradually after 1970s. In the urea method with urea as the raw material, the following chemical reaction is generated at a certain temperature and pressure or under the action of catalyst:

$$6(NH_2)_2CO \rightarrow (NH_2)_3C_3N_3 + 6NH_3 + 3CO_2$$

The above-mentioned synthesis process is generally divided into the following three types based on reaction conditions: high-pressure liquid-phase quenching method (7~100 MPa, 370~450° C.), low-pressure liquid-phase quenching method (0.6~1 MPa, 380~440° C.) and low-pressure gas-phase quenching method (<0.2 MPa, 390° C.). Compared to the processes by high-pressure liquid-phase quenching method and low-pressure liquid-phase quenching method, the said process by low-pressure gas-phase quenching method has such advantages as short flow, fewer equipment, weak medium corrosiveness, less investment and short construction period and hence has attracted broad attention and has been widely applied. As a matter of fact, the low-pressure gas-phase quenching method has achieved relatively rapid development in recent ten years and accounted for about 55% of total global melamine output.

The system for process by low-pressure gas-phase quenching method is shown in FIG. 1. The flow for such process in the prior art is disclosed in U.S. Pat. No. 4,451,271, CN1188761A and CN1493565A, including the following steps and operation parameters:

(a) Carrier gas pre-heating. The process gas from carrier gas compressor with pressure of 0.1~0.2 MPa is heated to 360~400° C. by using carrier gas pre-heater and high temperature molten salt. The heated process gas enters fluidized bed reactor as fluidized carrier gas.

(b) Chemical reaction. Urea melt at about 140° C. is pumped into the fluidized bed reactor with upper pressure of 0.05~0.1 MPa and temperature controlled within 390~400° C. Under the action of catalyst, about 85~90 wt % urea reacts chemically to generate melamine and corresponding volume of ammonia and $CO_2$ (i.e., reaction by-products, usually called tail gas in the industry) as per chemical equation. The generated melamine is gaseous and dissolves in carrier gas and tail gas. The catalyst can be porous alumina, monox, titanium oxide or aluminum silicate colloid. The reaction heat is provided by molten salt immersed in the heating tube of catalyst bed.

(c) Cooling of gas generated from reaction. Carrier gas and tail gas with dissolved melamine are exhausted from the top of fluidized bed, enter hot gas cooler tube side, and then get cooled to 310~320° C. by low-temperature organic heat carrying agent outside the tube. The high-boiling-point by-products (such as melam) in gases are precipitated by crystallization in the gas stream.

(d) Constant-temperature filtering. The gas from the hot gas cooler further flows into the hot gas filter shell side, enters the filter tube under the action of pressure differential, and gets purified with high-boiling-point by-products and catalyst particles intercepted outside by filtering medium. Filter cake attached outside the filter medium is blown down by the blowback gas and falls on the filter bottom and gets discharged regularly. In order to prevent melamine precipitation due to gas cooling in the filter, it is necessary to heat the filter to ensure constant-temperature filtering.

Hot gas cooling and filtering can cause scarring very easily, blocking tubes and equipment. Hence, there are 2 sets of equipment (1 for service and 1 for standby). This is one of the key technical points and difficulties of the low-pressure gas-phase quenching process.

(e) Gas-phase quenching crystallization. Hot gas at about 320° C. from the filter mixes with cold gas at about 140° C. from urea scrubber, and then gets further cooled to 180~220° C. At last, the melamine is precipitated by crystallization.

(f) Gas-solid cyclone separation. The melamine crystalline powder enters the melamine collector along with the gas stream to finish the gas-solid separation. The separated melamine is compressed out from the discharging equipment at the bottom and then gets delivered to the product packaging system.

(g) Process gas boosting. Process gas with melamine powder separated still contains ammonia, $CO_2$, melamine particles and small amounts of un-reacted reactants, and then enters urea scrubber after boosting by cold gas blower.

(h) Urea scrubbing and cooling. Process gas from the cold gas blower mixes with low-temperature urea melt from urea pump, flows downwards, and gets scrubbed and cooled by urea. Melamine particles and un-reacted reactants in the process gas enter the urea melt and get further cooled to about 140° C. The urea is heated to 136~140° C. and then the said urea melt is cooled to 127~130° C. by using cooler outside the scrubber.

(i) Gas-liquid separation. The gas-liquid mixture from the lower part of urea scrubber withstands the separation of urea and process gas by using specifically designed demister. The separated urea enters the kettle for circulation. Gas-liquid separation of urea scrubber is also one of the key technical points and difficulties of the gas-phase quenching process.

(j) Process gas distribution and circulation. Process gas separated by the gas-liquid separator contains crystallization cooling gas, reactor carrier gas and reaction by-product (tail gas). The crystallization cooling gas circulates from the lower part of crystallizer back to the crystallizer, and is used to cool the reaction gases; fluidized carrier gas circulates back to the reactor after boosting by carrier gas compressor and heating by carrier gas pre-heater, and is used as the fluidized carrier gas of catalyst; the tail gas (masses of $NH_3$ and $CO_2$ account for 50% respectively) is delivered to corresponding treating unit and output volume of tail gas can be adjusted automatically through process gas system pressure which is controlled at 0.01~0.05 MPa in general.

The said process by low-pressure gas-phase quenching method in the prior art still has the following technical defects:

First, the production efficiency per unit volume of the equipment is low. In the prior art, the process by low-pressure gas-phase quenching method is characterized by low operating pressure in melamine reactor, low partial pressure of reactant and slow chemical reaction, resulting in low production efficiency per unit volume of the equipment. For the purpose of higher yields, reactor with larger volume is needed. For example, the equipment with single line annual production capacity of 30,000t shall be provided with a fluidized bed reactor (with diameter more than 8 m) and a crystallizer. However, the design and construction of large-volume melamine equipment face high technical difficulties of equipment design and manufacturing and large investment. Hence, it is hard to achieve higher single line product capacity in the said process. Second, the product's power consumption is high. In the low-pressure gas-phase quenching method, since the equipment needs large amounts of circulating process gas and the pressure ratio is large, it is necessary to provide high-power carrier gas compressor and cold gas blower. Accordingly, the process consumes more power (no less than 1350 kwh for every ton of melamine in general).

Third, the cold gas blower cannot work stably over long period. In the existing process, the cold gas blower is placed behind the melamine collector, with saturated melamine process gas as the working medium. At the same time, the process gas also contains large amounts of melamine powder which has not been collected by cyclone separator. Affected by large centrifugal force of cold gas blower and body heat loss, the melamine can easily get attached to the gas channel and casing of the gas blower. Accordingly, thick melamine crystal scale is generated gradually, resulting in largely reducing the working efficiency and stability of the blower, shortening the continuous running period of the blower and equipment, and increasing the maintenance frequency and cost of the equipment.

Fourth, recycling or utilization cost of melamine tail gas (by-product) is high. In the process by low-pressure gas-phase quenching method, although the tail gas contains no water and can be utilized for many purposes, since the process gas system pressure can only reach 0.01~0.05 MPa, pressure of tail gas is correspondingly low and can be utilized only after re-boosting of tail gas. Besides, it is necessary to add turbine compressor or gas blower and hence power consumption and hardware investment are high.

DESCRIPTION OF THE INVENTION

The low-pressure gas-phase quenching method in the prior art faces such problems as low production efficiency per unit volume of the equipment, high product's power consumption, the cold gas blower's failing to work stably over long period and high recycling or utilization cost of melamine tail gas (by-product). In order to solve these problems, this invention provides a system and process for melamine production by gas-phase quenching method of energy efficient and cost saving type which features high production efficiency and good economic benefits.

Technical scheme for the system and process for melamine production by gas-phase quenching method of energy efficient and cost saving type in this invention is a system for melamine production by gas-phase quenching method, including:

A urea scrubber, after which a fluidized bed reactor, a hot gas cooler, a hot gas filter, a crystallizer and a melamine collector are installed in series successively, where the said melamine collector is connected to the said urea scrubber;

The said fluidized bed reactor is connected to a carrier gas pre-heater which is connected to a carrier gas compressor;

The said system for melamine production further comprises a gas-liquid separator connected to the said urea scrubber that is connected to the said crystallizer. The said carrier gas compressor is connected to the said gas-liquid separator;

A cold gas blower is provided between the said gas-liquid separator and the crystallizer.

A cold gas cooler is provided between the said cold gas blower and the said crystallizer.

The said carrier gas compressor is connected with the said gas-liquid separator via the said cold gas blower.

The said carrier gas pre-heater is a tubular heat exchanger.

The said hot gas filter is a bag filter.

The said hot gas cooler is connected to an exhaust boiler.

The said urea scrubber is provided with tubular evaporative heat exchanger.

The said gas-liquid separator is a cyclone demister.

A production process based on the said melamine production system, including the following steps:

(a) The carrier gas is compressed in carrier gas compressor until its pressure reaches 0.36~2.1 MPa and then the gas is heated in the carrier gas pre-heater to a temperature of 380~430° C. before flowing into the fluidized bed reactor as fluidized gas;

(b) Melamine synthesis: urea melt at 135~155° C. in the urea scrubber is pumped into the dense phase of catalyst in the fluidized bed reactor, where the reaction pressure is 0.3~1.9 Mpa and the temperature is 375~430° C. Urea reacts to produce reaction gases such as melamine, ammonia and $CO_2$.

(c) Cooling of reaction gases: the said reaction gases come out from the top of the fluidized bed reactor and flow into the hot gas cooler to be cooled to a temperature of 330~360° C., where high-boiling-point by-products are fully precipitated by crystallization in the gas stream;

(d) Filtering of reaction gases: the said reaction gases come out from the hot gas cooler and flow into the hot gas filter to be filtered. The said high-boiling-point by-products and catalyst particles are intercepted. The temperature in the said hot gas filter shall be higher than or equal to that of the reaction gases from the hot gas cooler, with temperature difference of no more than 3° C.;

(e) Melamine crystallization by gas-phase quenching: the reaction gases coming out from the filter flow into the crystallizer, where the gases mix with the crystallization cooling gas. The final temperature of the mixed gas shall be controlled within 210~230° C. The hot gases are quenched by cold gas and the majority of gaseous melamine is crystallized and precipitated from the reaction gases;

(f) Melamine crystal collection: the reaction gases mixed with melamine crystal flow into the melamine collector to finish gas-solid separation. The temperature in the said melamine collector shall be higher than or equal to that of gas-solid mixture from the melamine crystallizer, with temperature difference no more than 3° C.;

(g) Process gas cooling and purification: the reaction gases separated from melamine crystal flow out from the melamine collector and flow into the urea scrubber, where the gases mix with urea melt at 135~155° C., and then flow downward. The gases are scrubbed by the urea and get cooled. The melamine particles in process gas and un-reacted reactants are all held in the urea melt.

(h) Gas-liquid separation: the gas-liquid mixture which comes out from the lower part of the urea scrubber is separated by gas-liquid separator and then urea and process gas are generated. Part of the said urea is reused for circulation of scrubbing reaction gases and the rest is sent to the reactor for melamine synthesis.

(i) Process gas distribution: the process gas separated by the gas-liquid separator has a pressure of 0.15~1.8 Mpa, part of which is used as crystallization cooling gas and carrier gas and the rest is discharged as tail gas. After boosting by cold gas blower, the said crystallization cooling gas circulates back to crystallizer from the lower part of the crystallizer.

In Step (i), crystallization cooling gas from the said cold gas blower is cooled by the said cold gas cooler to 135~150° C., and then circulates back to crystallizer from the lower part of the crystallizer.

In Step (i), the said carrier gas enters the said carrier gas compressor after boosting by the said cold gas blower.

The said catalyst is particulate porous aluminum silicate colloid.

In Step (c), heat released when reaction gases in the said hot gas cooler get cooled is transferred to the exhaust boiler in which the medium is heated; or, the said released heat is transferred to the said carrier gas pre-heater to pre-heat the said carrier gas.

In Step (g), the heat released when reaction gases get cooled is taken away by tubular evaporative heat exchanger in the urea scrubber. The said heat exchanger tube has circulating saturated water whose evaporating temperature is 125~150° C.

In Step (h), the gas-liquid mixture from the lower part of the urea scrubber is separated by gas-liquid separator and then urea and process gas are generated. The said separated urea returns to the urea scrubber.

In Step (i), after being boosted by cold gas blower to 0.18-1.85 MPa, the said crystallization cooling gas circulates back to crystallizer from the lower part of the crystallizer.

As to production process in this invention, in Step (b) melamine synthesis: urea melt at 135~155° C. in the urea scrubber is pumped into the fluidized bed reactor, where the reaction pressure is 0.3~1.9 Mpa and the temperature is 375~430° C. Urea reacts to produce reaction gases such as melamine, ammonia and $CO_2$; in the reaction, since partial pressure of reactant is increased and chemical reaction rate is largely improved, about 90~99 wt % urea reacts chemically to generate melamine and corresponding volume of ammonia and $CO_2$ as per the chemical equation. The generated melamine is gaseous and dissolves in carrier gas and tail gas. In Step (c) cooling of reaction gases: the said reaction gases come out from the top of the fluidized bed reactor and flow into the hot gas cooler to be cooled, where high-boiling-point by-products are fully precipitated by crystallization in the gas stream; besides, final temperature of the cooled reaction gases in the hot gas cooler depends on partial pressures of high-boiling-point by-products and melamine. The temperature is within 330~360° C. In order to facilitate the cleaning of melamine and high-boiling-point by-product crystals, a tubular heat exchanger is preferred to be used as hot gas cooler. Heat released by process gas can be used to generate high grade water vapor through exhaust boiler or to pre-heat the reaction carrier gas in the first step. Temperature of reaction gas at the outlet of hot gas cooler can be controlled by adjusting the water level of exhaust boiler or the flow of reaction carrier gas.

Step (d) filtering of reaction gases: the said reaction gases come out from the hot gas cooler and flow into the hot gas filter to be filtered. The said high-boiling-point by-products and catalyst particles are intercepted. The temperature in the said hot gas filter shall be higher than or equal to that of the reaction gases from the hot gas cooler, with temperature difference of no more than 3° C.; the outlet temperature of the hot-gas filter must be kept the same as or little higher than the inlet temperature, to prevent the melamine crystallization and precipitation in the filtering process; the gas under the differential pressure enters the filter, with high-boiling-point by-products and catalyst particles intercepted outside, the reaction gas is purified. The filter cake attached outside the filter medium is blown down by the blowback gas and falls on the filter bottom; it shall be removed regularly. This invention prefers the bag filter as the hot-gas filter for purposes of effective on-line cleaning and regeneration. Additionally, as the preferred setting mode, it can install two sets of hot-gas cooler and filter, one is for the on-line cleaning, regeneration and standby while the other one is for operation.

Step (f) melamine crystal collection: the reaction gases mixed with melamine crystals flow into the melamine collector to finish gas-solid separation; the cyclone separator is chosen to be the melamine collector for the purpose of saving process gas operating pressure drop and equipment maintenance cost. To prevent the uncrystallized melamine gas from continuing to crystallize and bond to the wall in the melamine collector, the outlet gas temperature from the melamine collector must be kept the same as or little higher than the inlet gas temperature. For this purpose, the melamine collector needs heating and heat preservation to ensure that it can fulfill the process gas and gas-solid separation of melamine at a constant temperature from 210° C. to 230° C.

Step (g) process gas cooling and purification: the reaction gases separated from melamine crystals flow out from the melamine collector and flow into the urea scrubber, where the gases mix with urea melt at 135~155° C., and then flow downward. The gases are scrubbed by the urea and get cooled. The melamine particles in process gas and unreacted reactants all enter the urea melt, which makes the temperature drop from 210~230° C. to 155° C. The heat released by process gas cooling is carried away by the evaporative heat exchanger of the urea scrubber. The saturated water circulating inside of the heat exchanger tube shall and finally take the heat out of the process system through evaporation. To prevent production of crystal dirt on the heat exchanger by the urea, the temperature of preferred saturated water shall be 125~150° C.

Step (h) Gas-liquid separation: the gas-liquid mixture which comes out from the lower part of the urea scrubber is separated by gas-liquid separator and then urea and process gas are generated. Part of the said urea is reused for circulation of scrubbing reaction gases and the rest is sent to the reactor for melamine synthesis; as the preferred setting mode, the separated urea can return to the urea scrubber once again. This way, there is no need to set another urea storage device; the gas-liquid separator in this invention favors cyclone demister, which has advantages of high efficiency, low energy consumption and is maintenance-free.

Step (i) process gas distribution: part of the process gas separated by the gas-liquid separator is used as crystallization cooling gas and carrier gas and the rest is discharged as tail gas. After boosting by cold gas blower, the said crystallization cooling gas circulates back to crystallizer from the lower part of the crystallizer. The gas phase pressure of the whole process system in this invention can realize the automatic adjustment through the tail gas flow of discharging system. The preferred process gas pressure shall be stabilized at 0.15~1.8 MPa. The tail gas of discharging system will be sent to recycling and processing device. The carrier gas flow of reactor shall be controlled by adjusting the revolving speed of carrier gas compressor or/and inlet valve opening. The cold gas flow of crystallizer shall be controlled by adjusting the revolving speed of cold gas blower or/and inlet valve opening.

The advantages of the melamine production process by gas-phase quenching method of energy efficient and cost saving type in this invention are:

(1) The said melamine production process by gas-phase quenching method in this invention, shall raise the reaction pressure to 0.3~1.9 MPa. The system process pressure is raised to 0.15~1.8 MPa accordingly. It shall synchronously make relevant adjustment and design optimization for other process parameters and equipments. Through raising the reaction pressure, the reactant partial pressure in fluidized bed reactor can be raised. The chemical reaction speed of the urea-synthesized melamine increases greatly. Therefore it strengthens the capacity of per unit volume of each process equipment and reduces the volume of each process equipment. The single line productivity of production device can be further enlarged. Thus, it decreases the hardware investment and labor cost of unit melamine products. Compared with the existing similar process technology, the maximum productivity scale of which on a single line is 30,000t melamine per year because of the limit of pressure vessel design, manufacturing specified technology and cost limit, the process technology of this invention can smoothly realize an ultra-large scale of 120,000t melamine per year in the industry, while the hardware investment per ton of melamine is only 54~72% of that the existing technology. Meanwhile, it saves a great quantity of energy, because it has raised the process system pressure and decreased the gas compression ratio of the carrier compressor of fluidized bed reactor and the cold gas blower of melamine crystallizer, and so the gas compression work has been reduced greatly. Compared with the existing similar process technology, the power consumption of which per ton of melamine is in 1350~1560 kwh, the power consumption of the prior art per ton of melamine is in 400~1000 kwh. The power consumption has been decreased greatly. Compared with the low-pressure gas-phase quenching method process, this invention can expand the utilization of tail gas, simplify the process flow and decrease the hardware investment for tail gas process and energy consumption, because it has raised the system process gas pressure from 0.01~0.05 MPa to 0.15~1.8 MPa, which accordingly improves the pressure and energy grade of melamine gas tail. Therefore the melamine tail gas produced by the process technology of this invention is of higher economic value.

The melamine production process by gas-phase quenching method of this invention, not only raises the reaction pressure, but also adjusts accordingly a series of process parameters. It effectively improves the reaction rate, at the same time avoids by-products, difficulties in melamine separation and other problems caused by the simply increased reaction pressure. As a result the process is able to work normally and effectively.

(2) Since the system pressure has been raised, the melamine production process by gas-phase quenching method of this invention is provided with the conditions to place the cold gas blower between the process gas urea scrubbing and melamine crystal. The first advantage of the design is: The cold gas blower's inlet process gas temperature decreases from 180~220° C. to 135~155° C. and so it reduces gas volume at the gas inlet. Therefore, it further decreases the cold gas compression work and the power consumption; the second advantage is: The lower inlet process gas temperature reduces the work conditions of cold gas blower, which is good for reducing the mechanical faults of the blower; the third advantage is: It has removed the melamine crystal dirt of the cold gas blower in the existing process technology. As a result the blower and process devices can work stably with high efficiency, the device maintenance strength and cost can be decreased, and the device productivity can be improved.

(3) the melamine production process by gas-phase quenching method of this invention installs the cold gas cooler at the outlet of the cold gas blower. Since the temperature of the cold gas will increase after the cold gas is compressed by the cold gas blower, circulation volume of the crystallized cooling gas may be increased accordingly with the aim of crystallizing the gaseous melamine of the reaction gas. To solve this problem, the preferred method is to cool the cold gas to the inlet gas temperature of the blower by using evaporative cooler. So, it can reduce the circulation volume of cold gas. Compared with process without setting any cold gas cooler, the cold gas circulation system, because of this process, can improve and save energy by as much as 14~21%.

BRIEF DESCRIPTION OF THE DRAWINGS

To help improve understanding of the present invention, the said system and process for melamine production by gas-phase quenching method of energy efficient and cost saving type of the present invention are further elaborated in combination with the drawings and preferred embodiments.

DETAILED DESCRIPTION OF THE PREFERRED EMBODIMENTS

Embodiment 1

Figure 2:
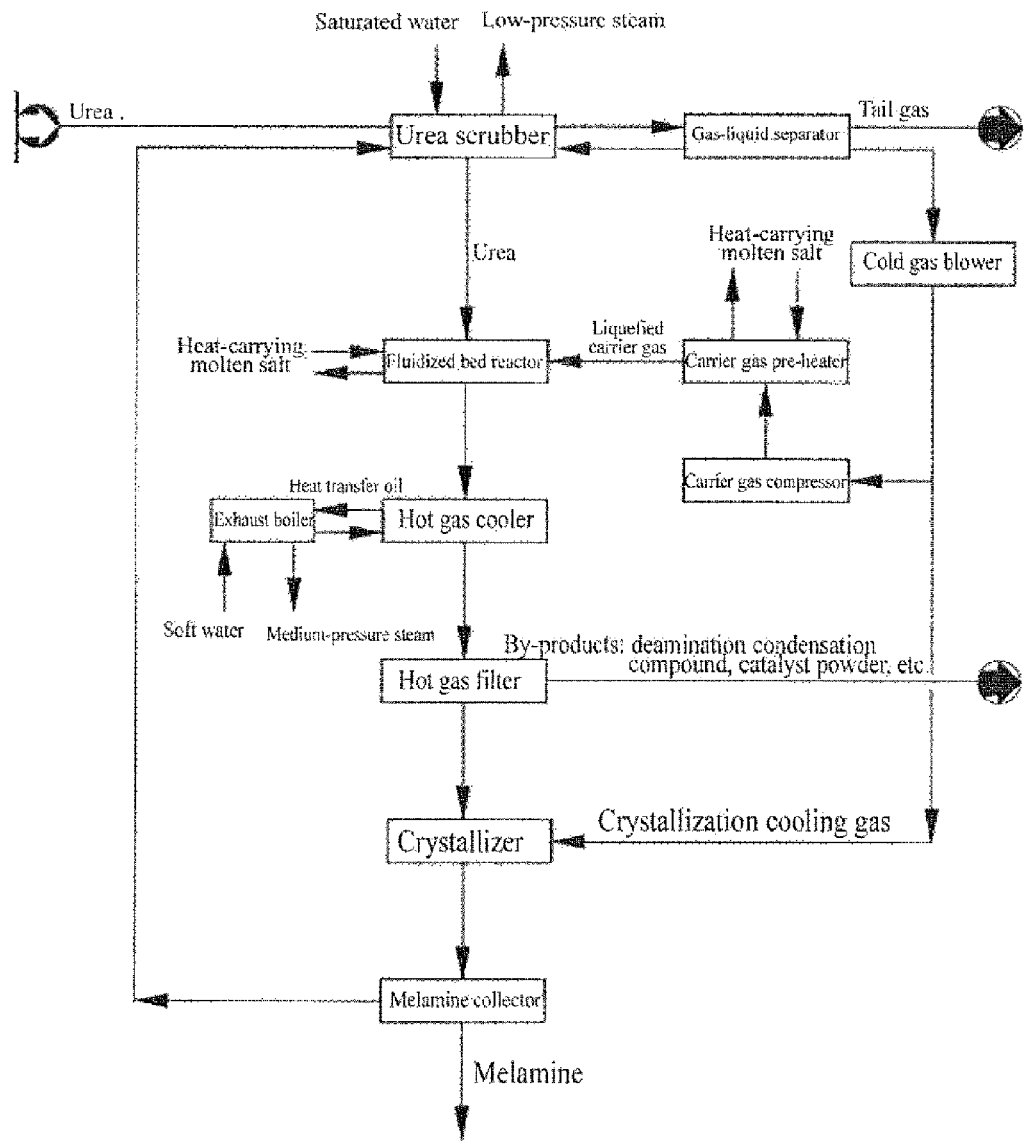
FIG. 2 is a schematic presentation of the system for melamine production by gas-phase quenching method, according to the present invention.

The system for melamine production by gas phase quenching method of this embodiment is shown in FIG. 2, comprising: A urea scrubber, after which a fluidized bed reactor, a hot gas cooler, a hot gas filter, a crystallizer and a melamine collector are installed in series successively, where the said melamine collector is connected to the said urea scrubber, wherein, the said hot gas cooler in this embodiment is multi-tube cooler. The said fluidized bed reactor is connected to a carrier gas pre-heater which is connected to a carrier gas compressor; The said system for melamine production further comprises a gas-liquid separator connected to the said urea scrubber that is connected to a crystallizer. The said gas-liquid separator in this embodiment is a wire mesh demister using inertia and is connected to the said carrier gas compressor via a cool gas blower.

A cool gas blower is provided between the said gas-liquid separator and the crystallizer.

Production process of the said system for melamine production by gas phase quenching method in this embodiment is as follows:

(a) Carrier gas is compressed by the carrier gas compressor with a pressure of 0.36 MPa and is heated to 380° C. with the carrier gas pre-heater, then it is sent to fluidized bed reactor as fluidized carrier gas;

(b) Melamine synthesis: urea melt at 135° C. in the urea scrubber is pumped into the dense phase of catalyst of the fluidized bed reactor, where the pressure is 0.3 Mpa and the temperature is 375° C. Urea reactions produce reaction gases such as melamine, ammonia and $CO_2$. The aid catalyst in this embodiment is porous colloidal alumina particles.

(c) Cooling of reaction gases: reaction gases come out from the top of fluidized bed reactor and flow into the hot gas cooler to the temperature of 330° C., where high-boiling-point by-products is separated through crystallization to the maximum;

(d) Filtering of reaction gases: reaction gases come out from the hot gas cooler and flow into the hot gas filter, where the said high-boiling-point by-products and catalyst particles are intercepted. The temperature in the said hot gas filter shall be maintained at 330° C.;

(e) Melamine crystallization by gas-phase quenching: reaction gases which come out from the filter flow into the crystallizer, where the gases are mixed with cooling air. The final temperature of the mixed air shall be controlled within 180° C. so that the hot gases are cooled and the majority of gas melamine is crystallized and separated;

(f) Melamine crystal collection: reaction gases mixed with melamine crystal flow into the melamine collector, where the melamine crystal is separated from other gases. Constant temperature in the said melamine collector shall be kept at 210° C.;

(g) Process gas cooling and purification: the reaction gases separated from melamine crystal flow out from the melamine collector and flow into the urea scrubber, where the gases are mixed with 135° C. urea melt, and then flows downward. The gases are scrubbed and cooled by the urea. The melamine particles in process gas and un-reacted substances are all held in the urea melt.

(h) Gas-liquid separation: gas-liquid mixture which comes out from the bottom of the urea scrubber is separated with gas-liquid separator so that urea and process gas are generated. The urea separated is sent to urea storage pool. Part of the said urea is reused for circulation of scrubbing reaction gases and the rest is sent to the reactor for melamine synthesis.

(i) Process gas distribution: process gas from the gas-liquid separator has a pressure of 0.15 Mpa part of which is used as cooling air for crystallization and the rest is discharged as tail gas, wherein pressure of the said cooling air for crystallization rises to 0.18 MPa in cool-air blower and flow back to crystallizer through its bottom. The said carrier gas enters carrier compressor after being boosting by the said cool-air blower.

Embodiment 2

Figure 3:
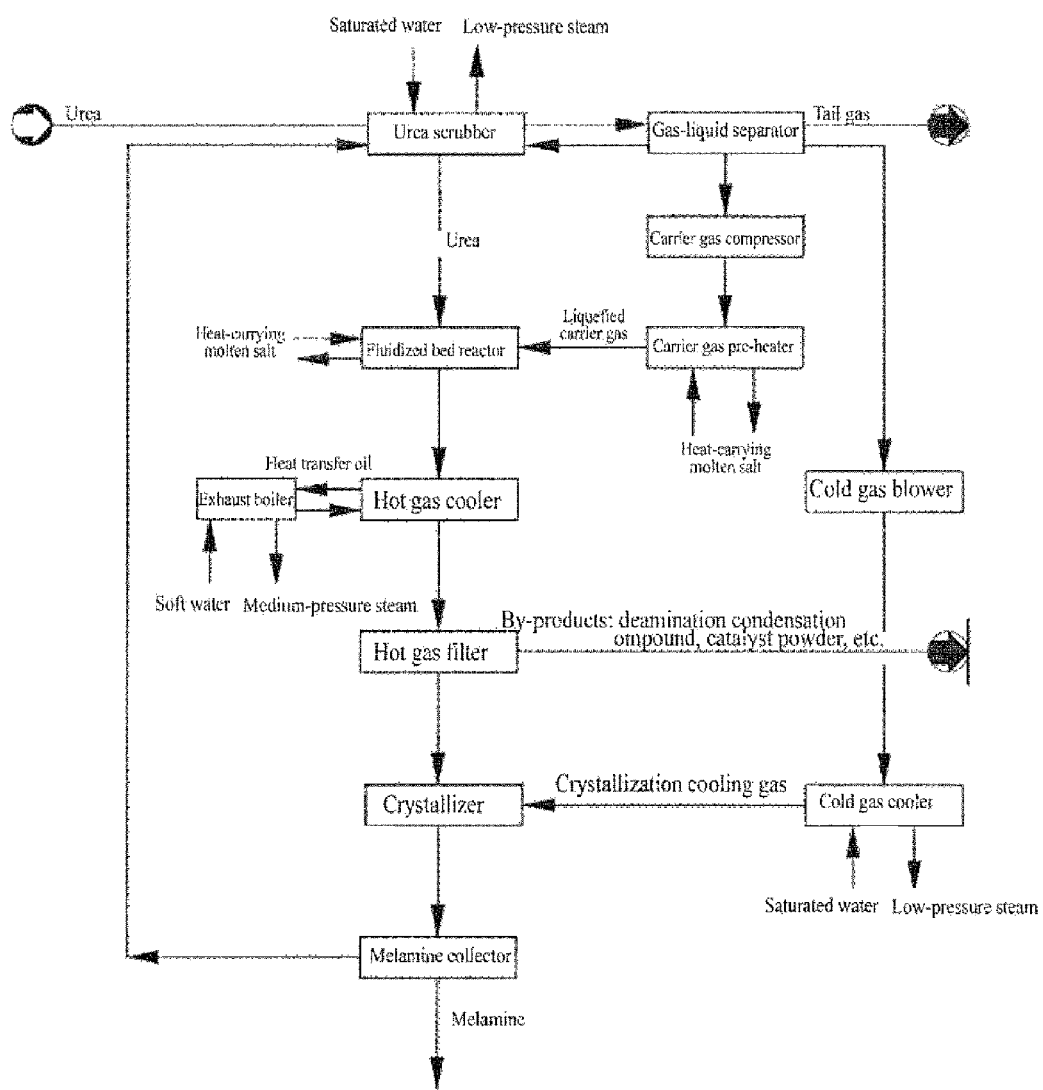
FIG. 3 is a schematic presentation for convertible mode of the system for melamine production by gas-phase quenching method, according to the present invention.

The system for melamine production by gas phase quenching method of this embodiment is shown in FIG. 3, comprising: A urea scrubber, after which a fluidized bed reactor, a hot gas cooler, a hot gas filter, a crystallizer and a melamine collector are installed in series successively, where the said melamine collector is connected to the said urea scrubber. The said hot gas cooler in this embodiment is connected to exhaust boiler. The said fluidized bed reactor is connected to a carrier gas pre-heater which is connected to a carrier gas compressor, wherein the carrier gas pre-heater in this embodiment is tubular heat exchanger;

The said system for melamine production further comprises a gas-liquid separator connected to the said urea scrubber that is connected to the said crystallizer. The said carrier gas compressor is connected to the said gas-liquid separator;

A cool-air blower is provided between the said gas-liquid separator and the said crystallizer, and an evaporative cold air cooler with saturated water is provided between the said cool-air blower and the said crystallizer as well.

The said hot gas filter in this embodiment is a metal fiber bag type filter and an evaporative heat exchanger with saturated water is provided in the said urea scrubber.

The said gas-liquid separator in this embodiment is cyclone demister.

Production process of the said system for melamine production by gas phase quenching method in this embodiment is as follows:

(a) The carrier gas is compressed in carrier gas compressor until its pressure reaches 2.1 MPa and then the gas is heated in the carrier gas heater to 430° C. before flowing into the fluidized bed reactor as fluidized gas. (b) Melamine synthesis: urea melt at 155° C. in the urea scrubber is pumped into the dense phase of catalyst of the fluidized bed reactor, where the pressure is 1.9 Mpa and the temperature is 430° C. Urea reactions produce reaction gases such as melamine, ammonia and $CO_2$. The said catalyst in this embodiment is porous colloidal aluminum silicate particles.

(c) Cooling of reaction gases: reaction gases come out from the top of fluidized bed reactor and flow into the hot gas cooler to the temperature of 360° C., where high-boiling-point by-products is separated through crystallization to the maximum;

(d) Filtering of reaction gases, reaction gases come out from the hot gas cooler and flow into the hot gas filter, where the said high-boiling-point by-products, deammoniated concentrates and catalyst powder particles are intercepted. The temperature in the said hot gas filter shall be maintained at 362° C.;

(e) Melamine crystallization by gas-phase quenching, reaction gases which come out from the filter flow into the crystallizer, where the gases are mixed with cooling air. The final temperature of the mixed air shall be controlled at 230° C. so that the hot gases are cooled and the majority of gas melamine is crystallized and separated;

(f) Melamine crystal collection, reaction gases mixed with melamine crystal flow into the melamine collector, where the melamine crystal is separated from other gases. Constant temperature in the said melamine collector shall be kept at 230° C.;

(g) Process gas cooling and purification, the reaction gases separated from melamine crystal flow out from the melamine collector and flow into the urea scrubber, where the gases are mixed with 155° C. urea melt, and then flows downward. The gases are scrubbed and cooled by the urea. The melamine particles in process gas and un-reacted substances are all held in the urea melt.

(h) Gas-liquid separation, gas-liquid mixture which comes out from the bottom of the urea scrubber is separated with gas-liquid separator so that urea and process gas are generated. The urea separated is sent to urea storage pool. Part of the said urea is reused for circulation of scrubbing reaction gases and the rest is sent to the reactor for melamine synthesis;

(i) Process gas distribution, process gas from the gas-liquid separator has a pressure of 1.8 Mpa part of which is used as cooling air for crystallization and the rest is discharged as tail gas, wherein pressure of the said cooling air for crystallization rises to 1.85 MPa in cool-air blower and flow back to crystallizer through its bottom after cooling to 150° C. in the said cold air cooler.

The heat released by cooling of reaction gases generated in step (g) is carried away by the evaporative heat exchanger of the urea washing tower. With saturated water cycling inside of the heat exchanger tube, the heat is finally taken out of the process system with the evaporation of the water. Evaporating temperature of the saturated water is 135° C.

Embodiment 3

System for melamine production by gas phase quenching method in this embodiment is identical to that in Embodiment 2.

Production process of the said system for melamine production by gas phase quenching method in this embodiment is as follows:

(a) The carrier gas is compressed in carrier gas compressor until its pressure reaches 0.5 MPa and then the gas is heated in the carrier gas heater to the temperature of 400° C. with reaction gases and high temperature molten salt successively before flowing into the fluidized bed reactor as fluidized gas.

(b) Melamine synthesis, urea melt at 140° C. in the urea scrubber is pumped into the dense phase of catalyst of the fluidized bed reactor, where the pressure is 0.4 Mpa and the temperature is 380° C. Urea reactions produce reaction gases such as melamine, ammonia and $CO_2$. The said catalyst in this embodiment is porous colloidal aluminum silicate.

(c) Cooling of reaction gases: the said reaction gases come out from the top of the fluidized bed reactor and flow into the hot gas cooler to be cooled to the temperature of 340° C., where high-boiling-point by-products are fully precipitated by crystallization in the gas stream; heat released from said hot gas cooler is transferred to the carrier gas pre-heater and preheat carrier gas.

(d) Filtration of reaction generated gases: reaction generated gases come out from the hot-air cooler and flow into the hot-air filter, where the said high-boiling-point-point by-products and catalyst particles are intercepted. The temperature in the said hot-air filter shall be maintained at 340° C.;

(e) Melamine crystallization by gas-phase quenching, reaction generated gases which come out from the filter flow into the crystallizer, where the gases are mixed with cooling air. The final temperature of the mixed air shall be controlled at 210° C. so that the hot gases are cooled and the majority of gas melamine is crystallized and separated;

(f) Melamine crystal collection, reaction generated gases mixed with melamine crystal flow into the melamine collector, where the melamine crystal is separated from other gases. Constant temperature in the said melamine collector shall be kept at 213° C.;

(g) Process gas cooling and purification, the reaction gases separated from melamine crystal flow out from the melamine collector and flow into the urea scrubber, where the gases are mixed with 140° C. urea melt, and then flows downward. The gases are scrubbed and cooled by the urea. The melamine particles in process gas and un-reacted reactants are all held in the urea melt.

(h) Gas-liquid separation, gas-liquid mixture which comes out from the bottom of the urea scrubber is separated with gas-liquid separator so that urea and process gas are generated. The urea separated flow back to the urea scrubber. Part of the said urea is reused for circulation of scrubbing reaction generated gas and the rest is sent to the reactor for melamine synthesis.

(i) Process gas distribution: process gas from the gas-liquid separator has a pressure of 0.4 Mpa part of which is used as cooling air for crystallization and the rest is discharged as tail gas, wherein pressure of the said cooling air for crystallization rises to 0.43 MPa in cool-air blower and flows back to crystallizer through its bottom after cooling to 135° C. in the said evaporative cold air cooler. The heat released by cooling of reaction gases generated in step (g) is carried away by the evaporative heat exchanger of the urea washing tower. With saturated water cycling inside of the heat exchanger tube, the heat is finally taken out of the process system with the evaporation of the water. Evaporating temperature of the saturated water is 150° C.

In the said embodiments above, heating unit is provided for the hot gas filter and melamine collector to maintain a desired temperature, which is common sense for technicians of this sector and is not detailed here. Furthermore, bag-type filters are used in the said embodiments above as hot gas filter, wherein any applicable filtering medium in the prior art can be used for filter bags of the bag-type filter, such as heat-resistant glass fiber felt (cloth) or anti-corrosion metal fiber felt (cloth) against process fluid. The said filter may adopt any applicable microporus filter in the prior art as optional embodiments.

Embodiment for Comparison

Figure 1:
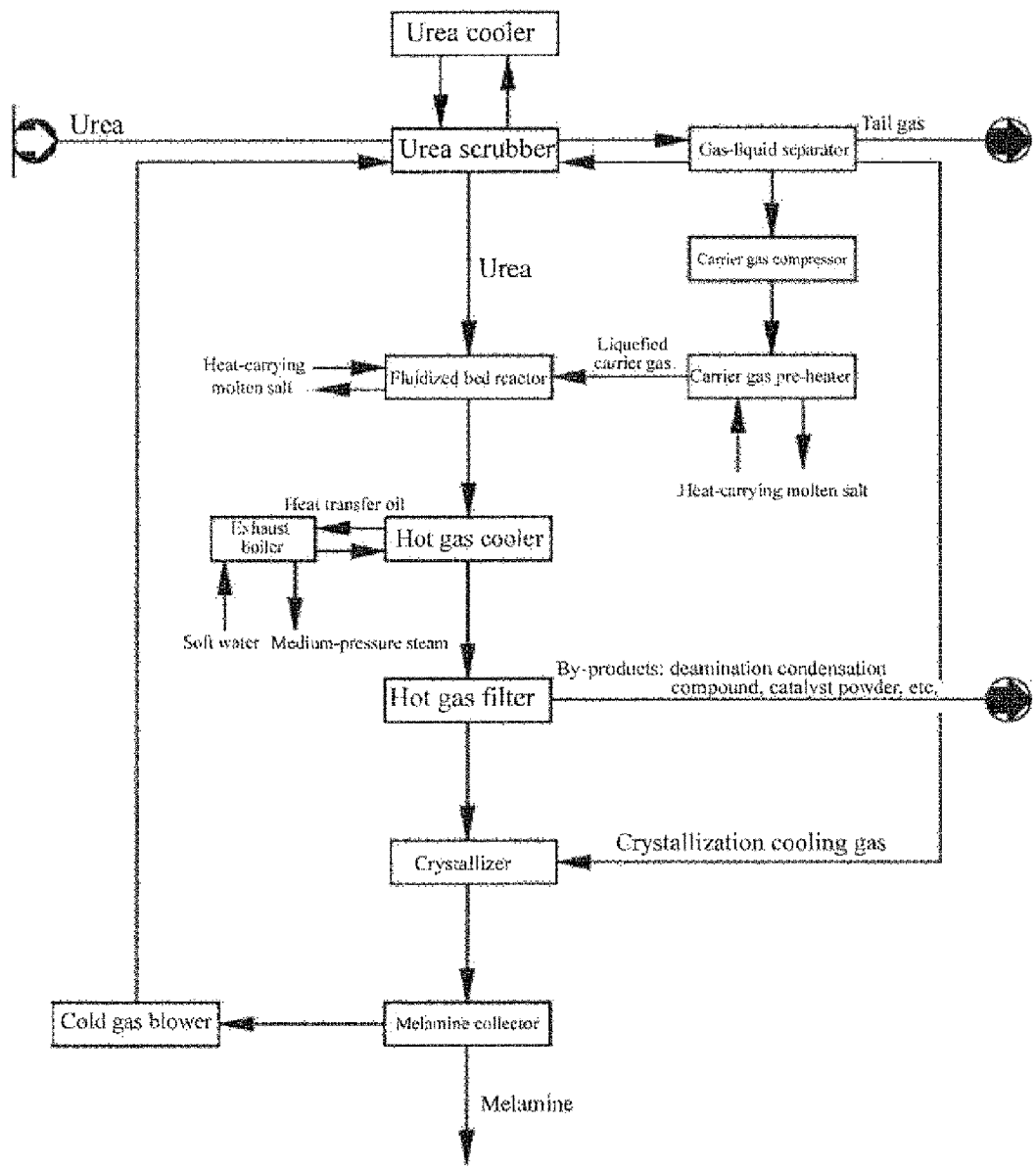
FIG. 1 is a schematic presentation of regular system for melamine production by gas-phase quenching method.

For the purpose of proving that the system and process for melamine production by gas-phase quenching method of the present invention has advantageous technical effects compared to the prior art, further description of technical effects of the present invention is made as follows in combination with actual productive results of the embodiments and the embodiment for comparison, wherein the said embodiment for comparison adopts the process of low-pressure gas-phase quenching method in the prior art of which the system diagram is shown in FIG. 1. Actual measured process parameters and effects of the said embodiments and the embodiment for comparison is shown in the following table:

|  | Embodiment 1 | | Embodiment 2 | | Embodiment 3 | | Embodiment for comparison | |
| --- | --- | --- | --- | --- | --- | --- | --- | --- |
|  | Temperature (° C.) | Pressure (Mpa) | Temperature (° C.) | Pressure (Mpa) | Temperature (° C.) | Pressure (Mpa) | Temperature (° C.) | Pressure (MPa) |
| Process gas system | — | 0.15 | — | 1.8 | — | 0.4 | — | 0.02 |
| Fluidized bed reactor (outlet) | 375 | 0.22 | 430 | 1.9 | 395 | 0.5 | 395 | 0.09 |
| Hot gas cooler (outlet) | 330 | — | 360 | — | 340 | — | 320 | — |
| Hot gas filter (outlet) | 330 | 0.17 | 362 | 1.83 | 340 | — | 320 | 0.03 |
| Melamine crystal (outlet) | 210 | — | 230 | — | 210 | — | 200 | — |
| Melamine collector (outlet) | 210 | — | 230 | — | 213 | — | 200 | — |

|  | Embodiment 1 | | Embodiment 2 | | Embodiment 3 | | Embodiment for comparison | |
|---|---|---|---|---|---|---|---|---|
|  | Temperature (°C.) | Pressure (Mpa) | Temperature (°C.) | Pressure (Mpa) | Temperature (°C.) | Pressure (Mpa) | Temperature (°C.) | Pressure (MPa) |
| Urea scrubber (outlet) | 135 | — | 155 | — | 140 | — | 140 | 0.02 |
| Gas-liquid separator (outlet) | 135 | 0.15 | 155 | 1.8 | 140 | — | 140 | 0.02 |
| Carrier gas compressor inlet | — | 0.17 | 155 | 1.8 | 140 | 0.4 | 140 | 0.02 |
| outlet | — | 0.35 | — | 2.1 | — | 0.6 | — | 0.18 |
| Carrier gas pre-heater (outlet) | 380 | — | 430 | — | 400 | — | 400 | — |
| Cool-air blower inlet | — | 0.15 | 155 | 1.8 | 140 | 0.4 | 200 | 0.01 |
| outlet | — | 0.17 | — | 1.85 | — | 0.43 | — | 0.04 |
| Cold air cooler (outlet) | None | | 150 | — | 135 | — | None | |
| Process parameters of melamine tail gas | 135 | 0.15 | 155 | 1.8 | 140 | 0.4 | 140 | 0.02 |
| Power consumption of melamine per ton | 900-970 kwh | | 410-430 kwh | | 500-550 kwh | | 1480-1560 kwh | |
| Investment ratio of equipment with annual production capacity of 60,000 t | 0.72 (completed with 1 production line) | | 0.54 (completed with 1 production line) | | 0.6 (completed with 1 production line) | | 1.0 (completed with 1 production line) | |

According to the table, it is evident that, in the process of the embodiment for comparison, power consumption of melamine per ton and investment ratio of equipment with annual production capacity of 60,000t are far greater than those in the process of Embodiment 1-3, in addition, 2 production lines are needed in the embodiment for comparison. Therefore, it can be seen that compared to the system and process for melamine production by gas-phase quenching method of in the prior art, the system and process for melamine production by gas-phase quenching method of the present invention has the advantages of high productivity, long operational cycle, low investment for equipment, low energy consumption, high utility value of tail gas, good economic returns and better technical effects.

It will be evident to those skilled in the art that the invention is not limited to the details of the foregoing illustrated embodiments and all changes of forms or details which come within the meaning and range of the claims are therefore intended to be embraced therein.

The invention claimed is:

1. A system for melamine production by gas-phase quenching method, including:
   a urea scrubber, after which a fluidized bed reactor, a hot gas cooler, a hot gas filter, a crystallizer and a melamine collector are installed in series successively, where the melamine collector is connected to the urea scrubber;
   wherein the fluidized bed reactor is connected to a carrier gas pre-heater that is connected to a carrier gas compressor;
   wherein the system for melamine production further comprises a gas-liquid separator connected to the urea scrubber that is connected to the crystallizer, and the carrier gas compressor is connected to the gas-liquid separator; and
   wherein a cold gas blower is provided between the gas-liquid separator and the crystallizer.

2. The system for melamine production according to claim 1, wherein a cold gas cooler is provided between the cold gas blower and the crystallizer.

3. The system for melamine production according to claim 1, wherein the carrier gas compressor is connected to the gas-liquid separator via the cold gas blower.

4. The system for melamine production according to claim 1, wherein the carrier gas pre-heater is a tubular heat exchanger.

5. The system for melamine production according to claim 4, wherein the hot gas filter is a bag filter.

6. The system for melamine production according to claim 5, wherein the hot gas cooler is connected to an exhaust boiler.

7. The system for melamine production according to claim 6, wherein the urea scrubber is provided with tubular evaporative heat exchanger.

8. The system for melamine production according to claim 7, wherein the gas-liquid separator is a cyclone demister.

9. A production process for melamine, including the following steps:
   (a) compressing a carrier gas in a carrier gas compressor to a pressure of 0.36~2.1 MPa and then heating the carrier gas in a carrier gas pre-heater to a temperature of 380~430° C., followed by flowing the carrier gas into a fluidized bed reactor as a fluidized gas;
   (b) pumping urea melt at a temperature of 135~155° C. in a urea scrubber into a dense phase of catalyst in the fluidized bed reactor, where the reaction pressure is 0.3~4.9 MPa and the temperature is 375~430° C., and reacting the urea melt to produce reaction gases including melamine, ammonia and $CO_2$;
   (c) passing the reaction gases out from a top of the fluidized bed reactor and into a hot gas cooler, and cooling the reaction gases to a temperature of 330~360° C., wherein high-boiling-point by-products are fully precipitated by crystallization in the gas stream;
   (d) filtering the reaction gases that come out from the hot gas cooler and flow into a hot gas filter, and intercepting the high-boiling-point by-products and catalyst particles, wherein the temperature in the hot gas filter is higher than or equal to that of the reaction gases from the hot gas cooler, with temperature difference of no more than 3° C.;

(e) flowing the reaction gases coming out from the hot gas filter into the crystallizer, mixing the gases with a crystallization cooling gas, a final temperature of the mixed gas being controlled to within 210~230° C., and quenching the hot gases by cold gas, wherein a majority of gaseous melamine is crystallized and precipitated from the reaction gases;

(f) flowing the reaction gases mixed with melamine crystal into a melamine collector, wherein a temperature in the melamine collector is higher than or equal to that of gas-solid mixture from a crystallizer, with temperature difference of no more than 3° C.;

(g) flowing the reaction gases separated from melamine crystal out from the melamine collector and into the urea scrubber, and mixing the gases with the urea melt at 135~155° C., flowing the mixture downward, scrubbing the gases with the urea and cooling the melamine particles in a process gas, wherein un-reacted reactants are held in the urea melt;

(h) separating the gas-liquid mixture that comes out from a lower part of the urea scrubber by a gas-liquid separator to form a process gas having a pressure of 0.15 to 1.8 MPa, thereby generating urea and the process gas, wherein part of the urea is reused for circulation of scrubbing reaction gases and the rest of the urea is sent to the reactor for melamine synthesis;

(i) using a portion of the process gas separated by the gas-liquid separator as a crystallization cooling gas and carrier gas and the rest of the process gas is discharged as tail gas, and after boosting by a cold gas blower, circulating the crystallization cooling gas back to the crystallizer from a lower part of the crystallizer.

10. The production process according to claim 9, wherein in Step (i), crystallization cooling gas from the cold gas blower is cooled by a cold gas cooler to 135~150° C., and then circulates back to crystallizer from the lower part of the crystallizer.

11. The production process according to claim 9, wherein in Step (i), the said carrier gas enters the said carrier gas compressor after being boosted by the cold gas blower.

12. The production process according to claim 9, wherein the catalyst is a particulate porous aluminum silicate colloid.

13. The production process according to claim 9, wherein in Step (c), heat released when reaction gases in the hot gas cooler get cooled is transferred to an exhaust boiler in which the medium is heated; and the released heat is transferred to the carrier gas pre-heater to pre-heat the carrier gas.

14. The production process according to claim 9, wherein in Step (g), the heat released when reaction gases get cooled is taken away by a tubular evaporative heat exchanger in the urea scrubber, the tubular heat exchanger tube having circulating saturated water with an evaporating temperature of 125~150° C.

15. The production process according to claim 9, wherein in Step (h), the gas-liquid mixture from the lower part of the urea scrubber is separated by the gas-liquid separator, thereby generating urea and process gases, and then the part of the urea separated by the gas-liquid separator is returned to the urea scrubber.

16. The production process according to claim 9, wherein in Step (i), after being boosted by the cold gas blower to 0.18-1.85 MPa, the crystallization cooling gas circulates back to crystallizer from the lower part of the crystallizer.

* * * * *